United States Patent [19]
Cote

[11] Patent Number: 5,551,940
[45] Date of Patent: Sep. 3, 1996

[54] APPARATUS FOR SEPARATING AGGREGATES FROM AN ASPHALT-AGGREGATE MIXTURE

[75] Inventor: Michael M. Cote, Hampden, Me.

[73] Assignee: The Lane Construction Corporation, Meriden, Conn.

[21] Appl. No.: 498,931

[22] Filed: Jul. 6, 1995

[51] Int. Cl.$^6$ ............................. B04B 13/00; B04B 11/04
[52] U.S. Cl. .................... 494/11; 494/30; 73/866
[58] Field of Search ........................ 494/1, 5, 6, 7, 494/10, 11, 23, 27, 30, 36, 60, 64, 85, 901; 73/866, 865.5; 422/72, 101; 208/45

[56] References Cited

U.S. PATENT DOCUMENTS

| 3,203,253 | 8/1965 | Scheid | 73/865.5 |
|---|---|---|---|
| 3,524,353 | 8/1970 | Bors | 73/865.5 |
| 3,686,959 | 8/1972 | Kruiger | 73/866 |

*Primary Examiner*—Charles E. Cooley
*Attorney, Agent, or Firm*—Frederick R. Cantor, Esq.

[57] ABSTRACT

A centrifuge is utilized to extract asphalt from a test sample containing asphalt and dispersed aggregates, so that the sample can be analyzed for asphalt content, and aggregate particle size distributions. Organic solvent, water and liquid soap are fed sequentially (selectively) into a rotatable bowl in the centrifuge for dissolving the asphalt, emulsifying solvent films on the aggregate, and rinsing soap film off of the aggregate particles. The quantities of solvent, water and liquid soap are controlled by a programmable controller containing a microprocessor, such that the asphalt extraction process is accomplished automatically, with minimum consumption of solvent, liquid soap and water. The controller can be reprogrammed as necessary to achieve different operational cycles, based on experience and test sample variations.

7 Claims, 1 Drawing Sheet

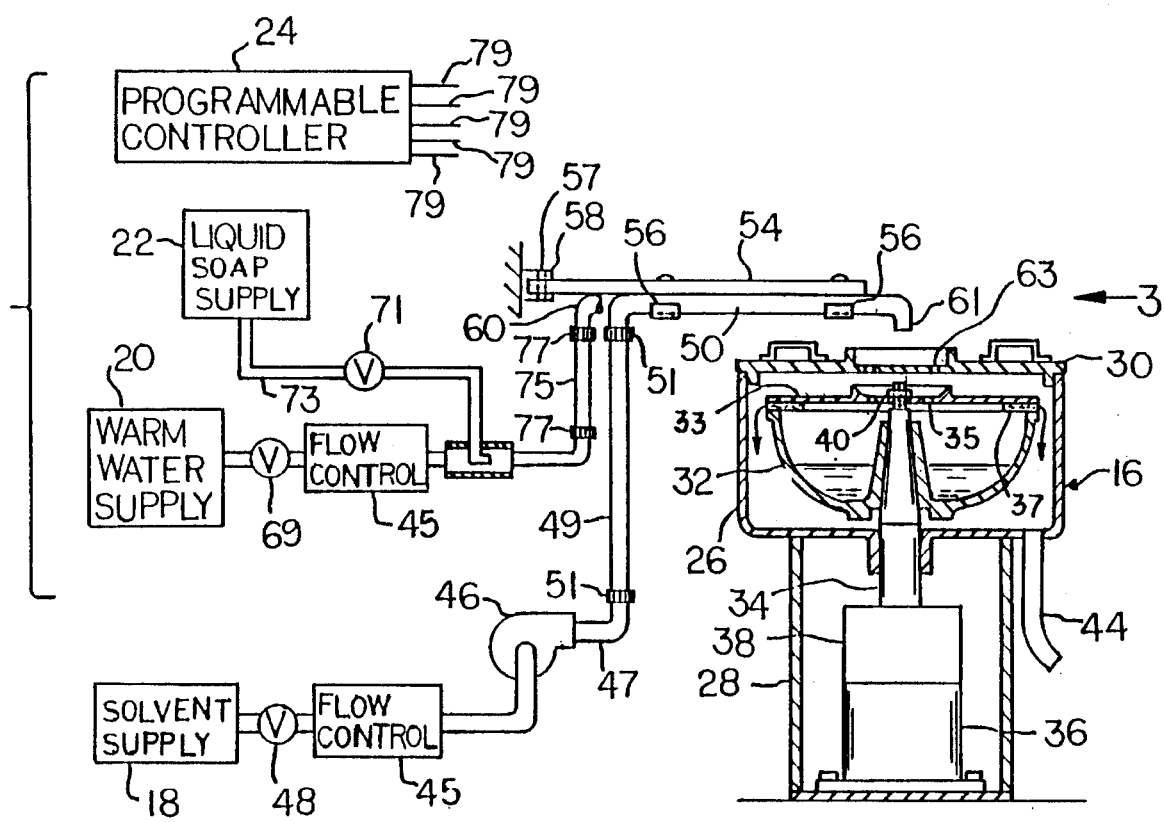

APPARATUS FOR SEPARATING AGGREGATES FROM AN ASPHALT-AGGREGATE MIXTURE

BACKGROUND OF THE PRESENT INVENTION

SUMMARY OF THE PRESENT INVENTION

This invention relates to an apparatus for separating aggregates from an asphalt-aggregate mixture. Such separation is useful as part of a procedure for testing the mixture for asphalt content and particle size distribution in the mixture. Such testing is performed as a quality control function in the process of formulating and building asphalt pavement.

Conventional asphalt pavement commonly comprises a prepared subgrade (or foundation soil), a base layer on the subgrade, and asphalt surface layer laid on the base layer. The base layer can comprise an asphalt-aggregate mixture, or compacted aggregates (without the asphalt); typically the base layer is at least three inches thick when asphalt is used therein, and at least six inches thick when no asphalt is used. The aggregates in the base layer typically will have maximum diameters in the range of from one-half inch to about one and one-half inch.

The asphalt surface layer will typically have a thickness of about one inch. The aggregates (rocks) in the surface layer will have somewhat smaller maximum diameters, from about three-quarters inch to about one-quarter inch.

The asphalt and aggregates are mixed together until the aggregates are individually coated with the asphalt. The mixing operation is carried out with both the aggregates and asphalt preheated, in order to dry the aggregates and thereby prevent moisture from existing within the final mix. The mixing operation is commonly termed a hot mix batching operation.

The hot mixture is transported to the area where the pavement is to be laid, and spread in a partially compacted layer to a reasonably uniform surface condition. While the mixture is still hot a heavy roller is run over the surface a number of times to compact the mixture and form a smooth surface. The same procedure is used for the asphalt-aggregate base layer, and for the asphalt aggregate surface layer.

The proportion of aggregate to asphalt is kept within limits, based on experience and job specifications. Also, by controlling the aggregate particle size distribution and the asphalt content, the percentage of voids in the mixture is kept within limits. Typically, the acceptable void percentage is in the range of from three to four percent. When the void percentage is higher than six to eight percent, the pavement may deteriorate prematurely.

In order to verify the properties of the asphalt-aggregate mixture, test samples are taken at various times in the process, e.g., after a batch mixing operation at the mixing facility, or from a section of pavement at the pavement site. Testing of the asphalt-aggregate sample involves extracting the asphalt from the aggregate.

The testing operation can take various different forms and practices. However, in one particular procedure the weight of the test sample is recorded, after which the sample is placed in a centrifuge to extract the asphalt from the aggregate. Organic solvent will be added to the centrifuge to dissolve the asphalt, such that the dissolved asphalt (in liquid form) can be drained out of the centrifuge, through a filter, leaving the bare aggregate in the centrifuge. Warm water is then added to the aggregate to remove the solvent from the aggregate. The water removes the solvent and it is drained out of the centrifuge through a filter.

The bare aggregate is removed from the bowl and dried in an oven to remove water from the aggregate surface. The aggregate is then weighed.

The asphalt-extraction process, in conjunction with the weighing operations, enables the technician to determine the asphalt content of the sample. The size range of the aggregates can be determined by passing the bare aggregates through a range of different square mesh size sieves.

The present invention is concerned with an economical and efficient apparatus for extracting asphalt from an aggregate-asphalt mixture, as part of the aforementioned testing process.

The apparatus comprises a timer-controlled valve system for delivering predetermined quantities of organic solvent, soap and water to the centrifuge such that the aggregate-asphalt mixture in the centrifuge is subjected automatically to a series of cleaning (asphalt extraction) activities. The apparatus times the activities and the quantities of solvent, soap and water, so that the process becomes standardized and automatic; the human element, and the possibility of human error and miscalculations, is eliminated, so that the asphalt extraction process is quicker, more efficient and reliable.

In preferred practice of the invention, the timing and control functions are accomplished with a programmable controller, e.g. TEXAS INSTRUMENTS model 315 Central Processing Unit, or a corresponding processor manufactured by the SIEMENS COMPANY.

When a programmable controller is used for the timing and controlling function, the cycle can be altered or changed to meet different conditions, e.g. different sample sizes, different solvents, and different asphalt qualities and quantities.

The principal aim of the invention is to carry out the asphalt extraction procedure more efficiently and quickly, with reduced expenditures for solvents and soaps, and with minimum human involvement in the process. Further features of the invention will be apparent from the attached drawings and description of a preferred embodiment of the invention.

In summary, and in accordance with the above-discussion, the foregoing objectives are achieved in the following embodiments.

1. Apparatus for extracting asphalt from an asphalt-aggregate mixture, comprising:

a centrifuge that includes a rotary bowl, an electric motor for rotating said bowl around a vertical axis, and a drain for the flow of liquid out of said centrifuge;

an organic solvent supply source having a first electrical control means;

a warm water supply source having a second electrical control means;

a liquid soap supply source having a third electrical control means;

means for delivering solvent from said solvent source to said bowl;

means for delivering water and scrap from said water and soap sources to said bowl; and a timer means having separate plural outputs connected to said motor, first control means, second control means, and third control means; whereby the solvent, water and soap can be cyclically delivered to the rotatable bowl, and dissolved asphalt can be drained out of the bowl on an automatic timed cycle.

2. The apparatus, as described in paragraph 1, wherein said timer means is a programmable controller.

3. The apparatus, as described in paragraph 1, wherein said timer means provides at least one solvent soak activity, at least one soapy wash activity, and at least one clean water rinse activity for the asphalt-aggregate mixture in said bowl.

4. The apparatus, as described in paragraph 3, wherein said timer means provides a liquid drain action after each solvent soak activity, soapy wash activity, and water rinse activity.

5. The apparatus, as described in paragraph 1, wherein said solvent delivery means comprises a liquid conduit having a downwardly-directed discharge spout;

means for swinging said liquid conduit in a horizontal arc between an inactive position offset laterally from said centrifuge, and an active position overlying the centrifuge; and said discharge spout being operable to direct solvent into said bowl when said liquid conduit is in its active position.

6. The apparatus, as described in paragraph 1, wherein said water and soap delivery means comprises a liquid conduit having a downwardly-directed discharge spout;

means for swinging said liquid conduit in a horizontal arc between an inactive position offset laterally from said centrifuge, and an active position overlying the centrifuge; and said discharge spout being operable to direct water and soap downwardly into said bowl when said liquid conduit is in its active position.

7. The apparatus, as described in paragraph 1, and further comprising a horizontal arm;

means pivotably supporting said arm for swinging motion in a horizontal plane between a standby position offset from the centrifuge and an operating position overlying the centrifuge;

said solvent delivery means comprising a first liquid conduit extending along said arm, said conduit having a liquid inlet near said pivot support means and a downwardly-directed discharge spout remote from said pivot support means;

said water and soap delivery means comprising a second liquid conduit extending along said arm, said second conduit having a liquid inlet near said pivot support means and a downwardly-directed discharge spout remote from said pivot support means; and each said conduit being operable to discharge liquid downwardly into said bowl when said art is in its operating position.

8. The apparatus, as described in paragraph 7, and further comprising a first flexible hose connected to the inlet on said first conduit, and a second flexible hose connected to the inlet on said second conduit, whereby said hoses are enabled to deliver liquids to the respective conduits without preventing horizontal swinging motion of said arm.

A BRIEF DESCRIPTION OF THE DRAWINGS

FIG. 1, is a fragmentary sectional view, taken through a typical asphalt roadway (pavement) according to conventional practice.

FIG. 2, is a view, partly schematic, showing an asphalt-extraction apparatus of the present invention. Such an apparatus can be used in conjunction with the process of building the asphalt pavement depicted in FIG. 1.

FIG. 3, is a fragmentary end view of a liquid delivery mechanism used in the FIG. 2 apparatus. FIG. 3 is taken in the direction of arrow 3 in FIG. 2.

DESCRIPTION OF A PREFERRED EMBODIMENT OF THE PRESENT INVENTION

FIG. 1, is a fragmentary sectional view, taken through a typical asphalt roadway (pavement) according to conventional practice.

Referring to FIG. 1, there is shown a section of pavement, comprising a prepared subgrade 10, an asphalt base 12, and asphalt surface layer 14. Subgrade 10 can be compacted earth having a relatively smooth surface. Base 12 layer can be a mixture of asphalt and non-porous rock (or aggregate); the aggregate and asphalt are mixed together by a hot-mix batching operation, such that each aggregate particle is preferably coated with asphalt.

Surface layer 14 can be an asphalt-aggregate mixture generally similar to the mixture used for base 12, except that the aggregates are somewhat smaller in size (i.e. finer). The proportion of asphalt to aggregate can be different in the base layer 12 and the surface layer 14. Also, the base layer 12 will usually have a greater thickness than the surface layer 14. In each layer, i.e. 12 or 14, the percentage of voids (vacant spaces) will be kept to a minimum, preferably no more than about four (4) percent of the layer volume.

Base 12 has tensile and compressive strengths to resist the wheel loadings and maintain the structural integrity of the pavement against degradation, break up, and distortion. Surface layer 14 has smoothness, distortion-resistance, and non-porosity (to resist water penetration).

FIG. 2, is a view, partly schematic, showing an asphalt-extraction apparatus of the present invention. Such an apparatus can be used in conjunction with the process of building the asphalt pavement depicted in FIG. 1.

FIG. 3, is a fragmentary end view of a liquid delivery mechanism used in the FIG. 2 apparatus. FIG. 3 is taken in the direction of arrow 3 in FIG. 2.

The present invention concerns an apparatus (as shown in FIGS. 2 and 3) for extracting asphalt from an asphalt-aggregate mixture, whereby the mixture can be tested for its physical properties, e.g. asphalt content, and aggregate particle size distribution. Referring to FIG. 2, the illustrated apparatus comprises a centrifuge 16, organic solvent supply 18, warm water supply 20, liquid soap supply 22, and programmable controller 24. The controller 24 operates, or controls, the electrical motor in the centrifuge 16, as well as valves associated with the solvent supply, warm water supply, and liquid soap supply, whereby an asphalt-aggregate mixture in the centrifuge 16 can be subjected to a series of timed cleaning (extracting) activities or events.

Centrifuge 16, as shown in the drawings, comprises an outer stationary shell, or tub, 26 supported on an upstanding columnar support structure 28. A removable cover 30 is provided to close the tub 26 when the centrifuge is running (rotating).

The centrifuge 16 includes a rotary bowl 32 carried on a vertical shaft 34 that extends through the bottom wall of shell 26. A vertical axis variable speed electric motor 36 is provided in columnar support structure 28 for delivering rotary power to shaft 34; a speed control potentiometer (not shown) is provided to set the desired bowl 32 rotational speed, or range of bowl 32 speeds.

Bowl 32 preferably has a detachable connection with shaft 34, such that the bowl 32 is removable from shell 26 at conclusion of the asphalt-extraction operation. The bowl 32, with the bare aggregates therein, can be placed in an oven to remove (or vaporize) liquid films from the aggregate (granule) surfaces, prior to weighing the bowl 32 (and contents) to determine the weight of the aggregate. As shown in the drawing, shaft 34 has a threaded section adapted to receive a torque nut 40, whereby the bowl 32 is removably secured to shaft 34 and the nut is tightened to a predetermined effective torque value.

Bowl 32 is provided with a lid 33 that is retained on the bowl 32 by torque nut 40. A series of holes 35 is provided in the lid 33 for delivering liquid to the bowl 32. Liquid supply pipes 50 and 60 have discharge spouts 61, 61 arranged to discharge liquids downwardly through holes 63 in cover 30, and then through holes 35 in lid 33, whereby the liquids are supplied to bowl 32.

An annular filter 37, containing & porous filtration media, is positioned between the upper edge of bowl 32 and the underside of lid 33, to permit flow of liquid out of the bowl 32 during each cleaning activity, while retaining the aggregates in the bowl 32. Torque nut 40 can be torqued to a desired setting, to control the force exerted by lid 33 on the filtration media, thereby providing some control on the filtration porosity and liquid flow rate out of the bowl 32. While the bowl 32 is rotating, liquids are forced centrifugally outwardly, so that such liquids are enabled to climb the bowl 32 side wall for escape through the filtration media. The filter 37 prevents aggregates from leaving the bowl 32. The aggregates are thus cleaned by contact with the various liquids.

The filter grade (porosity) is variable and selected so that substantially all aggregates in the sample are retained in the bowl 32. During a cleaning activity the cleaning liquid will occupy the bowl 32 and the surrounding annular space circumscribed by stationary shell 26. The ejected liquid and entrained (dissolved) asphalt solution drains through the drain line 44. The bowl 32 spin time is set to allow ample time for all liquid to exit the bowl 32 through the filter 37 before the bowl 32 is stopped and more liquid is added to the bowl 32 through the holes 63 in the center area of the cover 30 and the holes 35 in the center area of the lid 33.

The liquid solvent in solvent supply (tank) 18 may be any commercially available suitable organic solvent, e.g. a liquid obtainable from ROCHESTER MIDLAND COMPANY under the tradename NEUGENIC 4175. A motor-operated pump 46, in conjunction with an electrically operated valve 48, pumps solvent from source 18 through a rigid pipe 47 and flexible hose 49 into a horizontal conduit 50. A flow control device 45 is preferably provided for maintaining a desired flow rate through pipe 47 and hose 49, in spite of variations in solvent supply pressure. Consequently, controller 24 can operate on a time basis to regulate the quantity of solvent introduced to bowl 32 (by controlling the time period in which valve 48 is in the open condition). Hose 49 can be operatively connected to the pump outlet pipe and conduit 50, using screw-on couplings 51.

The use of a flexible hose 49 between the pump 46 and conduit 50 enables conduit 50 to be moved in a horizontal arc between an operating (active) position overlying the centrifuge 16, and a standby (inactive) position offset from the centrifuge 16. FIG. 2, shows conduit 50 in its active position overlying the centrifuge. FIG. 3, includes arrows 52, designating movement of the conduit 50 from the active position to the inactive (standby) position. The conduit can be moved manually in either direction, as shown by arrows 52.

Conduit 50 is suitably secured to a horizontal arm (or bar) 54 by means of clamps 56. As shown, conduit 50 is secured to the undersurface of arm 54. However, the conduit 50 can be secured to the upper surface of arm 54, if so desired.

The left end of arm 54 is swingably connected to a fixed bracket 58 by means of a vertical pivot pin 57, whereby the arm 54 can be manually swung in a horizontal arc around the pin 57 axis. Arm 54 supports conduit 50 and a second conduit 60, fragmentarily shown, that forms part of a system for delivering warm water and soap solution to the bowl 32 in centrifuge 16. Each conduit, 50 or 60, has a downwardly directed discharge spout 61 for directing the respective liquid (solvent, water or soapy solution) downwardly through openings 63 in cover 30, and openings 35 in lid 33, into bowl 32.

Warm water supply 20 can be a hot water tank adapted to deliver a pressurized stream of warm water into a warm water line 67; preferably a pressure regulator or equivalent flow control device 45 is provided in line 67 so that the water volumetric flow is proportioned to the flow duration time. An electrically-operated on-off valve 69 is provided in line 67 to control the water flow volume (as determined by the time interval in which the valve is in the open condition).

Valves 69 and 48 can be solenoid valves electrically controlled by programmable controller 24, whereby the quantity of water and solvent delivered to bowl 32 is controlled automatically by timing signals generated by controller 24. Ball valves, shown here as flow controls 45, can be used to temper the flow to a rate that the cover 30 and lid 33 holes, 63 and 35, can accommodate.

Liquid soap supply 22 can be a tank containing a quantity of liquid soap sufficient for a multiple number of asphalt extraction operations. The tank can be pressurized (e.g. with an accumulator) to maintain the liquid soap in a pressurized state. An electrically-operated valve (e.g. a solenoid valve) 71 is provided in a line 73 leading from soap supply 22 to the warm water line 67, whereby when valve 71 is in an open condition liquid soap will be injected into the water flowing through line 67. Valve 71 will be controlled by an electrical output from programmable controller 24, such that controller 24 determines the quantity of soap injected into line 67. The controller 24 thus determines the soap-water solution delivered through conduit 60 into bowl 32.

A second flexible hose 75 is connected between warm water line 67 and the aforementioned conduit 60, via screw-on couplings 77. FIG. 2, shows hose 75 offset to the left of hose 49. However, in an actual construction hose 75 could be located alongside hose 49, i.e. behind hose 49 in FIG. 2.

Conduits 50 and 60 can be substantially identical conduits clamped to arm 54 by clamps 56. Each conduit, 50 or 60, has an inlet end located near the pivot 57 and a discharge spout 61 located remote from pivot 57, whereby manual swinging motion of arm 54 around the pin 57 axis positions conduits 50 and 60 in the active condition, above the centrifuge, or in the standby condition, offset from the centrifuge. Arm 57 will be swung to the standby condition when it is desired to load a test sample into bowl 32, or when it is desired to remove bowl 32 from the shell 26.

Test samples are placed in bowl 37 manually (with cover 30 and lid 33 removed from shell 26 and lid 33 removed from bowl 32). The cover 30 can be latched to shell 26 with manual latches, not shown, after which a start switch associated with controller 24 can be operated to initiate the asphalt-extraction process. While the centrifuge 16 is running, the arm 54 and attached conduits 50 and 60 are in the active position overlying cover 30.

Controller 24 has a plurality of individual electrical outputs 79 connected to motor 36, solvent pump 46, and valves 48, 69 and 71, so that selective energization of outputs 79 can provide an operating cycle for the centrifuge 16. Pump 46 and the associated valve 48 can be operated from a single output signal from the controller so as to be in simultaneous operation.

Various different operational cycles can be used while still achieving a satisfactory asphalt-extraction action. One exemplary cycle can include:

1. solvent admission (valve 48, pump 46)
2. solvent soak (delay time)
3. bowl spin (motor 36 on continuously)(solvent draining, drain 44)
4. bowl coast (delay time)
5. second solvent extraction, repeating steps 1 through 4
6. soapy water admission (valves 69, 71)
7. wash soak (delay time)
8. bowl 32 spin and drain (motor 36, drain 44)
9. bowl 32 coast (delay time)
10. warm rinse admission (valve 69)
11. bowl 32 spin and drain (motor 36, drain 44)
12. water extractions, repeating steps 9 through 11

The duration of each activity in the overall operational cycle will be selected, or varied, by controller 24; i.e. by the duration of each individual output signal 79.

The controller 24 can be used to control the speed of motor 36, and the resultant centrifugal force on the materials in bowl 32, such that the cleaning liquids can be retained in the bowl 32, or exhausted out of the bowl 32, according to the desired activity.

If a programmable controller 24 is used to control the asphalt extraction process, then the duration of each activity component in the cycle can be changed while keeping the same overall cycle. The programmable controller 24 has a keyboard that includes keys for changing the controller outputs. Such changes in the cycle can be used, e.g. when the size or composition of the test sample changes, or when a particular solvent or soap solution does not produce the expected result. As regards the functions of the various liquid solutions; the organic solvent is for the purpose of dissolving the asphalt, the water-soap solution is used to remove solvent-asphalt film from the aggregates, and the warm water rinse is used to remove soap film from the aggregates.

A principal feature of the invention is that the process is automatic and relatively quick (once a cycle has been established, i.e. programmed). Minimal quantities of solvent and soap are required, while still achieving a quick and effective asphalt extraction action.

The present invention, described above, relates to an apparatus for separating aggregates from an asphalt-aggregate mixture. Features of the present invention are recited in the appended claims. The drawings contained herein necessarily depict structural features and embodiments of the apparatus for separating aggregates from an asphalt-aggregate mixture, useful in the practice of the present invention.

However, it will be appreciated by those skilled in the arts pertaining thereto, that the present invention can be practiced in various alternate forms and configurations. Further, the previous detailed descriptions of the preferred embodiments of the present invention are presented for purposes of clarity of understanding only, and no unnecessary limitations should be implied therefrom. Finally, all appropriate mechanical and function equivalents to the above, which may be obvious to those skilled in the arts pertaining thereto, are considered to be encompassed within the claims of the present invention.

What is claimed is:

1. Apparatus for extracting aggregates from an asphalt-aggregate mixture, comprising:

a centrifuge that includes a rotary bowl, an electric motor for rotating said bowl around a vertical axis, and a drain for the flow of liquid out of said centrifuge;

an organic solvent supply source having a first liquid line connectable to said bowl, and a first electrically-operated flow control means controlling flow through said first liquid line;

a warm water supply source having a second liquid line connectible to said bowl, and a second electrically-operated flow control means controlling flow through said second liquid line;

a liquid soap supply source having a third line for injecting liquid soap into said second liquid line, and a third electrically-operated flow control means controlling flow through said third line; and a timer means having a first electrical output connected to said first electrically-operated flow control means, a second electrical output connected to said second electrically-operated flow control means, a third electrical output connected to said third electrically-operated flow control means; and a fourth electrical output connected to said electric motor; and whereby solvent, water and soap can be cyclically delivered to the rotatable bowl, and dissolved asphalt can be drained out of the bowl on an automatic timed cycle.

2. The apparatus, as described in claim 1, wherein said timer means is a programmable controller.

3. The apparatus, as described in claim 1, wherein each output of said timer means is turnable to an off condition, such that said bowl can be maintained in a motionless condition, to achieve a solvent soak cycle, or soapy wash soak cycle, or clean water rinse cycle.

4. The apparatus, as described in claim 1, wherein said first liquid line comprises a liquid conduit (50) having a downwardly-directed discharge spout;

means for swinging said liquid conduit in a horizontal arc between an inactive position offset laterally from said centrifuge, and an active position overlying the centrifuge; and said discharge spout being operable to direct solvent into said bowl when said liquid conduit is in its active position.

5. The apparatus, as described in claim 1, wherein said second liquid line comprises a liquid conduit (60) having a downwardly-directed discharge spout;

means for swinging said liquid conduit in a horizontal arc between an inactive position offset laterally from said centrifuge, and an active position overlying the centrifuge; and said discharge spout being operable to direct water and soap downwardly into said bowl when said liquid conduit is in its active position.

6. The apparatus, as described in claim 1, and further comprising a horizontal arm (54);

means pivotably supporting said arm for swinging motion in a horizontal plane between a standby position offset from the centrifuge and an operating position overlying the centrifuge;

said first liquid line comprising a first conduit (50) extending along said arm, said conduit having a liquid inlet proximate to said pivotable support means and a first downwardly-directed discharge spout remote from said pivotable support means; and said second liquid line comprising a second liquid conduit (60) extending along said arm;

said second conduit having a liquid inlet proximate to said pivotable support means and a second downwardly-directed discharge spout remote from said pivotable support means; and each said conduit being operable to discharge liquid downwardly into said bowl when said arm is in its operating position.

7. The apparatus, as described in claim 6, wherein said first liquid line further comprises a first flexible hose (49) connected to the inlet on said first conduit;

said second liquid line comprising a second flexible hose (75) connected to the inlet on said second conduit, whereby said hoses are enabled to deliver liquids to the respective conduits without preventing horizontal swinging motion of said arm.

* * * * *